(12) United States Patent
Benson (10) Patent No.: US 9,352,172 B2
(45) Date of Patent: May 31, 2016

(54) USING A GUIDE MEMBER TO FACILITATE BRACHYTHERAPY DEVICE SWAP

(75) Inventor: Maria Benson, Boylston, MA (US)

(73) Assignee: Hologic, Inc., Bedford, MA (US)

(*) Notice: Subject to any disclaimer, the term of this patent is extended or adjusted under 35 U.S.C. 154(b) by 679 days.

(21) Appl. No.: 12/894,888

(22) Filed: Sep. 30, 2010

(65) Prior Publication Data

US 2012/0083646 A1 Apr. 5, 2012

(51) Int. Cl.
*A61N 5/00* (2006.01)
*A61N 5/10* (2006.01)
*A61M 25/01* (2006.01)

(52) U.S. Cl.
CPC .............. *A61N 5/1015* (2013.01); *A61M 25/01* (2013.01); *A61M 25/0169* (2013.01); *A61N 2005/1008* (2013.01)

(58) Field of Classification Search
CPC ...................... A61M 25/0067; A61M 25/0074; A61M 2025/0079; A61M 2025/0293; A61M 25/09; A61M 2025/09125; A61N 5/1015; A61N 2005/1008
USPC ........................................ 600/3, 7; 604/99.01
See application file for complete search history.

(56) References Cited

U.S. PATENT DOCUMENTS

| 5,336,178 A | 8/1994 | Kaplan et al. |
| 5,720,717 A | 2/1998 | D'Andrea |
| 6,013,038 A * | 1/2000 | Pflueger ........................ 600/585 |
| 6,056,702 A * | 5/2000 | Lorenzo ........................ 600/585 |
| 6,248,122 B1 * | 6/2001 | Klumb et al. ................. 606/194 |
| 6,443,912 B1 * | 9/2002 | Mazzola et al. .............. 600/585 |
| 6,652,441 B2 * | 11/2003 | Weinberger et al. ............. 600/3 |
| 7,955,246 B2 * | 6/2011 | Lubock et al. .................... 600/3 |
| 8,123,722 B2 * | 2/2012 | Chang et al. .................. 604/104 |
| 2003/0191491 A1 * | 10/2003 | Duane et al. .................. 606/194 |
| 2005/0059990 A1 * | 3/2005 | Ayala et al. ................... 606/192 |
| 2009/0093821 A1 * | 4/2009 | Edmundson .................. 606/108 |
| 2012/0046647 A1 * | 2/2012 | Matsukuma et al. ......... 604/528 |

* cited by examiner

*Primary Examiner* — Charles A Marmor, II
*Assistant Examiner* — Thaddeus Cox (57) ABSTRACT

A guide member facilitates a device swap for brachytherapy treatment. A cavity evaluation device is introduced during surgery such that a distal end of the device is disposed in a resected cavity of the patient. The cavity evaluation device includes a shaft in which is disposed an elongated guide member. In a subsequent out-patient procedure the cavity evaluation device is removed from the resected cavity. If a brachytherapy treatment is to be performed then the cavity evaluation device is removed without removing the elongated guide member such that position of a portion of the elongated guide member in the resected cavity is maintained relative to the resected cavity. An anchor member helps to maintain the position of the guide member. Introduction of a brachytherapy catheter is then facilitated by introducing the elongated guide member into an opening of the brachytherapy catheter and using the elongated guide member to guide the brachytherapy catheter to the resected cavity.

13 Claims, 9 Drawing Sheets

USING A GUIDE MEMBER TO FACILITATE BRACHYTHERAPY DEVICE SWAP

CROSS-REFERENCE TO RELATED APPLICATIONS

N/A

BACKGROUND OF THE INVENTION

The present invention is generally related to medical treatments, and more particularly to interstitial Brachytherapy. Malignant tumors are often treated by surgical resection to remove as much of the tumor as possible. Radiation therapy can then be used to target the residual tumor margin. The radiation therapy can be administered through various methods including external-beam radiation, stereotactic radiosurgery, and permanent or temporary brachytherapy. Brachytherapy is a radiation therapy in which a source of therapeutic rays is inserted into the body at or near a tumor or other proliferative tissue disease site. At least one breast brachytherapy radiation treatment begins with insertion of a cavity evaluation device into the resected cavity during the lumpectomy procedure. If it is later determined that the patient is to be given brachytherapy treatment then the cavity evaluation device is removed during an office visit and a brachytherapy catheter is inserted into the path through the tissue previously occupied by the cavity evaluation device. More particularly, the catheter shaft is inserted into the tissue so that a balloon disposed at the distal end of the shaft is positioned within the resected cavity. The balloon is then inflated and radioactive material is loaded into one or more lumens for delivery via the brachytherapy catheter. The brachytherapy catheter is removed upon completion of the treatment.

SUMMARY OF THE INVENTION

The present invention is predicated in-part on recognition that introducing a device such as a brachytherapy catheter into a path previously occupied by a device such as a cavity evaluation device can be difficult to perform as an out-patient procedure. Because the path is through soft tissue it can close rapidly and does not always accurately guide the brachytherapy catheter to the resected cavity.

In accordance with an aspect of the invention, a method for facilitating brachytherapy treatment comprises the steps of: positioning a first device such that a distal end of the first device is disposed in a resected cavity of the patient, the first device including a shaft in which is disposed an elongated guide member; removing the first device from the resected cavity without removing the elongated guide member such that position of a portion of the elongated guide member in the resected cavity is maintained relative to the resected cavity; and introducing a brachytherapy catheter by introducing the elongated guide member into an opening of the brachytherapy catheter and using the elongated guide member to guide the brachytherapy catheter to the resected cavity.

In accordance with another aspect of the invention, apparatus for facilitating brachytherapy treatment comprises: a shaft; a tip disposed at a first end of the shaft; an inflatable member disposed around the shaft; an inflation lumen which transfers fluid into and out of the inflatable member; and an opening in the tip which receives a separate elongated guide member, and via which the guide member can be introduced to soft tissue.

In accordance with another aspect of the invention, apparatus for facilitating brachytherapy treatment comprises: a shaft; a tip disposed at a first end of the shaft; an inflatable member disposed around the shaft; an inflation lumen which transfers fluid into and out of the inflatable member; at least one dosing lumen; and an opening in the tip which receives a separate elongated guide member, and through which the guide member slidably moves in order to guide the apparatus through soft tissue.

One advantage of the guide member is that it helps to guide the brachytherapy catheter to the resected cavity. Furthermore, the guide member helps to accurately position the brachytherapy catheter and associated dosing lumens within the resected cavity.

DETAILED DESCRIPTION

Figure 1:
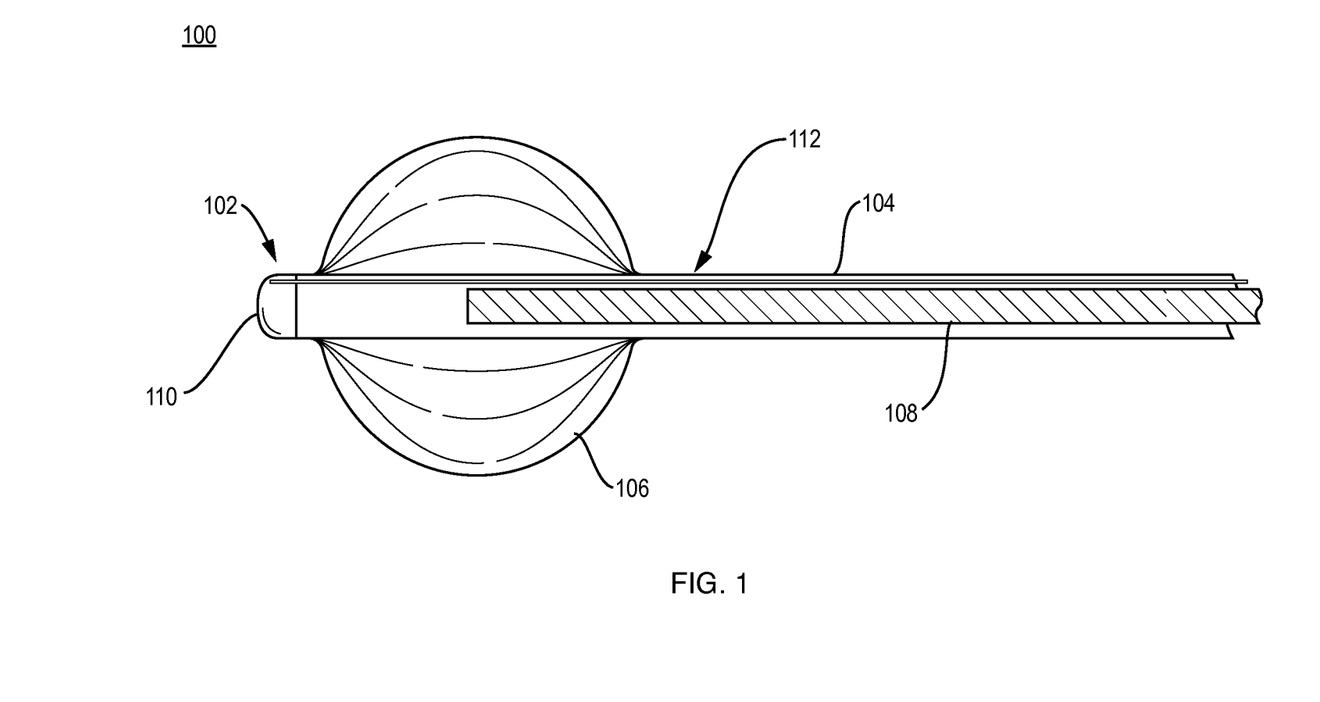
FIG. 1 illustrates a cavity evaluation device adapted to introduce a guide member.

FIG. 1 illustrates a medical device 100 adapted to introduce a guide member 102 into soft tissue to facilitate swapping of medical devices associated with a treatment such as interstitial brachytherapy, e.g., swapping a cavity evaluation device for a brachytherapy catheter. Device 100 may be a type of cavity evaluation device which includes a shaft 104, inflatable member 106, inflation lumen 108, and a tubular opening or lumen 112 for a separate guide member 102. The shaft is characterized by a proximal end (hub) and a distal end (tip 110). The inflation lumen is coupled at the proximal end to a connector (not illustrated). Once the device is positioned within the resected cavity the inflatable member is inflated, which helps maintain the device in position.

Figure 2:
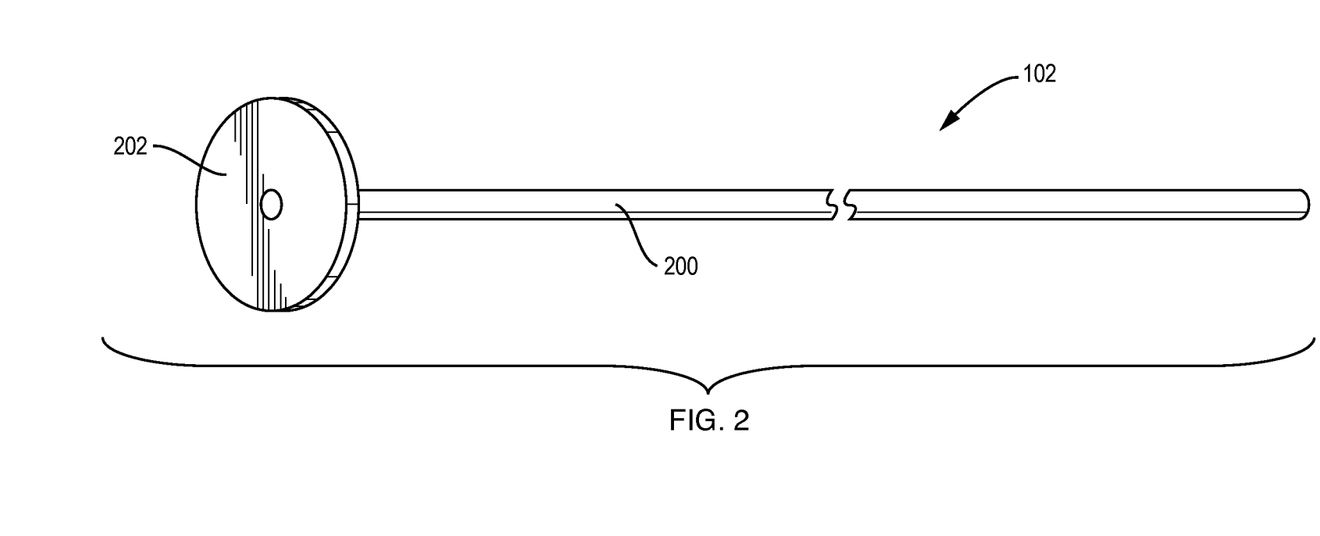
FIG. 2 illustrates an embodiment of a guide member.
Figure 3:
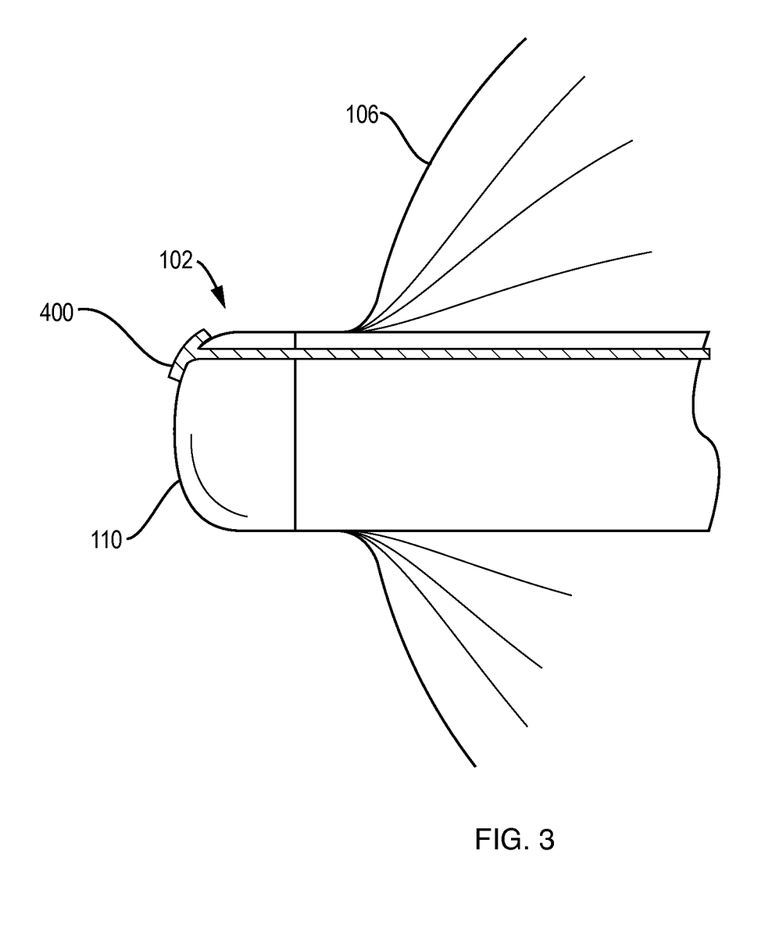
FIGS. 3 and 4 illustrate an alternative embodiment of the cavity evaluation device and guide member.
Figure 4:
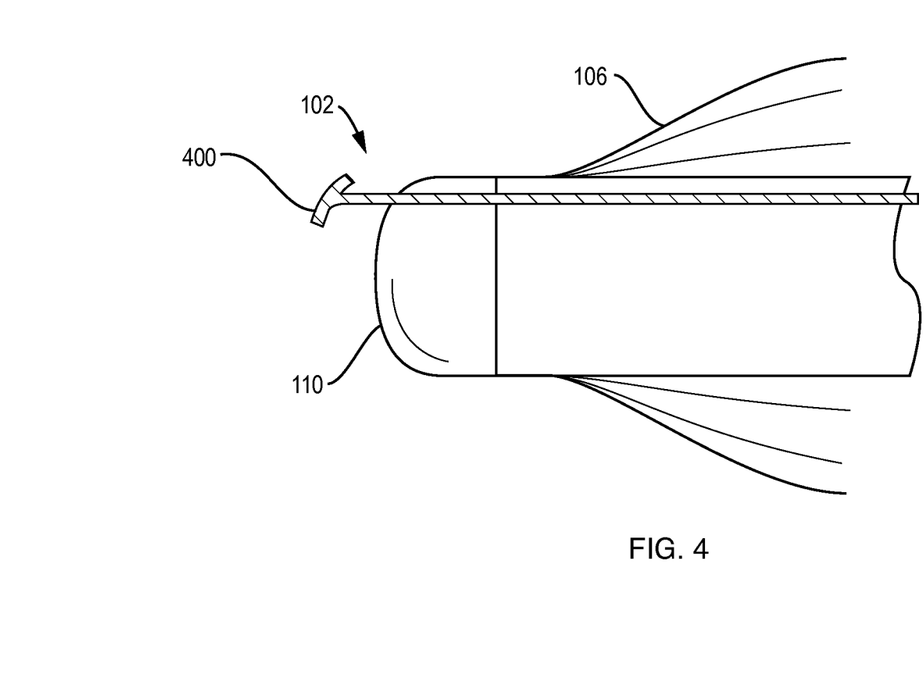

Referring to FIGS. 1 and 2, an opening in the tip 110 at the distal end of the shaft enables the elongated guide member 102 to be slidably moved into and out of the shaft 104. More particularly, the guide member 102 slides into or out of the tubular opening 112 formed in the shaft or a lumen disposed in the shaft. The guide member 102 includes a guide wire 200 and may also include an anchor member 202 at its distal end. The anchor member 202 helps to maintain the guide member 102 in a fixed position relative to surrounding tissue following introduction. This is accomplished by increasing resistance against the surrounding tissue to inhibit movement. The guide wire 200 and anchor member 202 may be made from a flexible material including but not limited to metallics such as nickel titanium (Nitinol), polyurethane, nylon, Polyether Block Amide (PEBA), Low-density polyethylene (LDPE), thermoplastic polyester elastomers, or PolyEtherEther-Ketone (PEEK). In one embodiment the guide wire and anchor member are imagable via various modalities based on sonic, electromagnetic or magnetic resonance imaging techniques. In the illustrated embodiment the anchor member 202 is disk-shaped and the guide wire 200 is attached at the center of the anchor member approximately perpendicular to a plane defined by the anchor member. However, those skilled in the art will recognize that the anchor member could have any of various alternative shapes and types of connection to the guide wire. For example, and without limitation, an anchor member 400 (FIGS. 3 and 4) may be characterized by a curvature that matches the portion of the tip 110 against which the anchor member will be disposed when loaded into device 100.

Referring now to FIGS. 1 through 6, the device 100 is pre-loaded with a guide member 102 before being introduced during the lumpectomy procedure. More particularly, the guide member 102 is introduced such that the distal end and inflatable member 106 are positioned within the resected cavity. Imaging equipment may be utilized to facilitate proper positioning. The inflatable member is then inflated by coupling the device to a source of pressurized fluid via connector. The inflation fluid flows into the inflatable member via the inflation lumen 108. One or more inflation holes (not shown) extend through the inflation lumen into the inflatable member. Once inflated, the inflatable member 106 helps to maintain the position of the device 100 with respect to the resected cavity. The connector is then detached from the fluid source and the device is left in place.

Figure 5:
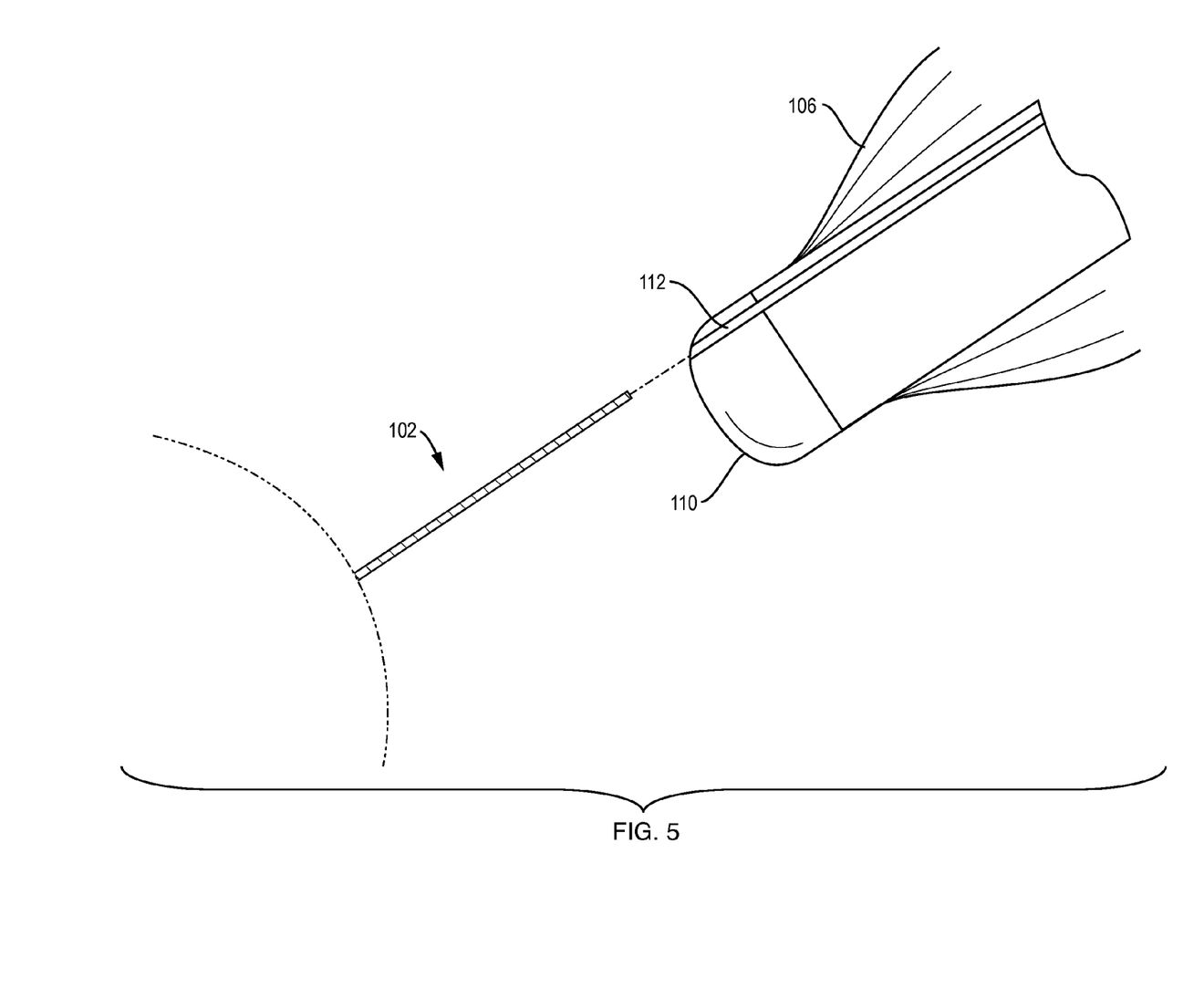
FIG. 5 illustrates withdrawal of the cavity evaluation device while guide member position is maintained.
Figure 6:
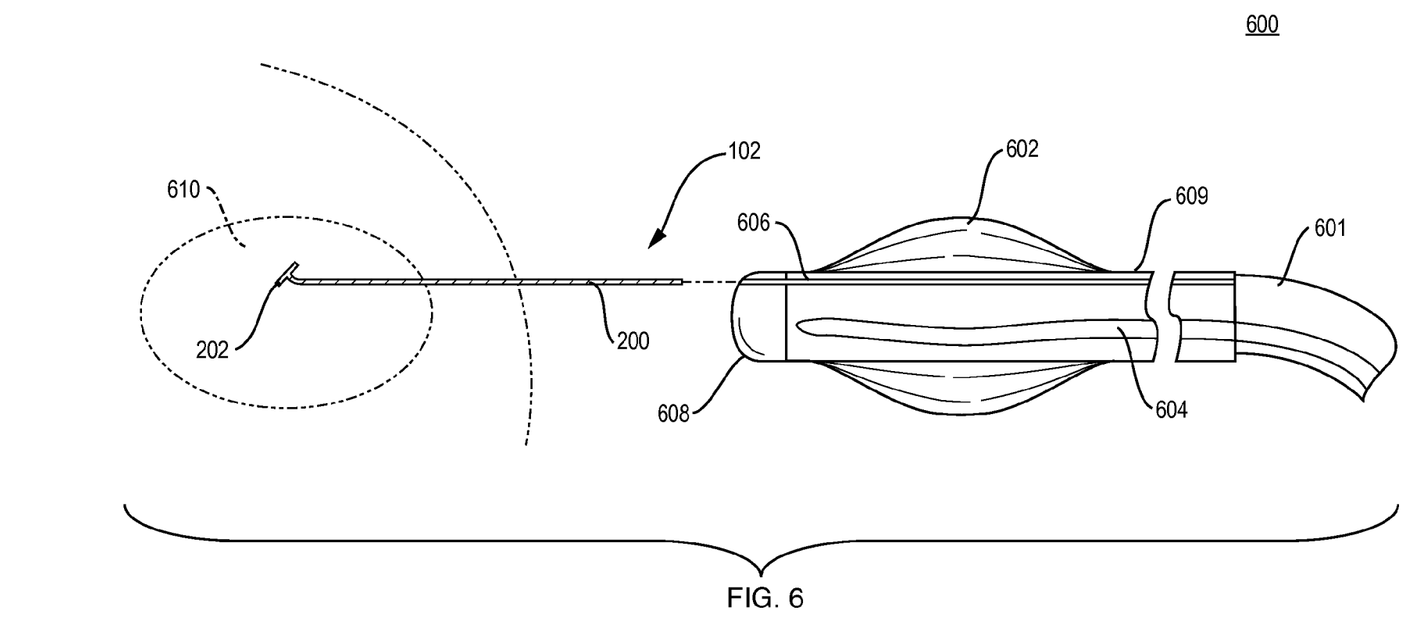
FIG. 6 illustrates use of a brachytherapy catheter adapted to utilize the guide member.

If it is later determined that the patient is to be given brachytherapy treatment then the device 100 is removed during an office visit and a brachytherapy catheter 600 with an inflatable member 602, such as a balloon, mounted on its distal end is inserted into the track through the tissue previously occupied by the cavity evaluation device 100. More particularly, the inflatable member 106 is deflated and the cavity evaluation device 100 is removed while the position of the guide member 102 relative to the resected cavity is maintained. Deployment of the guide member by creating separation between the anchor member 202 and the tip 110 (see FIG. 4) can help maintain the position of the guide member 102 during removal of the cavity evaluation device by, for example, preventing the anchor member from inadvertently latching onto or adhering to the tip. The guide member 102 may be deployed either before or after deflation of the inflatable member 106 by pushing on a free end of the guide wire. In either case, the inflatable member is deflated in order to permit removal of the cavity evaluation device. A portion of the guide wire 200 may extend out from the body of the patient following complete removal of the cavity evaluation device 100 in order to facilitate insertion of the guide wire into a receiver of the brachytherapy catheter shaft. It will be appreciated that the cavity evaluation device can alternatively be removed without deploying the guide member, i.e., removed along with the guide member, if necessary or desirable.

Referring now to FIG. 6, a flexible brachytherapy catheter 600 includes a flexible shaft 601, an inflatable member 602, at least one flexible dosing lumen 604, an inflation lumen (not illustrated), a guide lumen or tubular opening (collectively 606), a tip 608 and rigid section 609. Each dosing lumen 604 is sized to accommodate one or more radiation sources. The inflation lumen is coupled at a proximal end to a connector for introducing fluid for inflation. The lumens are made, for example, from a flexible material such as polyurethane, Nylon, Pebax, LDPE, Hytrel, or PEEK. Each dosing lumen 604 slidably extends through the flexible shaft and into openings which extend longitudinally into the rigid section 609. The openings in the rigid section are sized so that the exterior of each dosing lumen is tightly received in its respective opening. The lumens may be fixedly attached to the rigid section using an adhesive. The inflatable member functions in the same manner as the inflatable member of the device 100.

With the guide member 102 deployed (i.e. separated from the cavity evaluation device 100) and the device 100 removed from the patient, the guide wire 200 is used to facilitate introduction of the brachytherapy catheter device 600 by guiding the catheter through the existing opening in the soft tissue. As indicated above, the catheter shaft 601 includes a tip 608 with at least one opening 606 sized to receive the guide wire. Once inserted into the opening in the tip, the guide wire 200 is received by the associated lumen or tubular opening 606 as the brachytherapy catheter 600 is inserted into the soft tissue. Those skilled in the art will recognize that the flexibility of the guide wire 200 and resistance presented by the anchor member 202 in the soft tissue may be adjusted to achieve a desired result for a particular type of soft tissue, e.g., to present suitable resistance against movement. For example, the anchor member could be inflatable. The brachytherapy catheter 600 is eventually moved slidably along the guide wire to the extent that the tip 608 of the brachytherapy catheter contacts the anchor member 202, thereby indicating completion of that part of the procedure and helping to assure proper positioning of the brachytherapy catheter and associated dosing lumens with respect to the resected cavity 610. The inflatable member 602 is inflated after the tip of the catheter contacts the anchor member. The dosing lumens 604 are then used to deliver radiation therapy as already known in the art. The guide member 102 may be removed along with the brachytherapy catheter 600 once the treatment is completed. Alternatively, the guide member may be left in place if desired.

Figure 7:
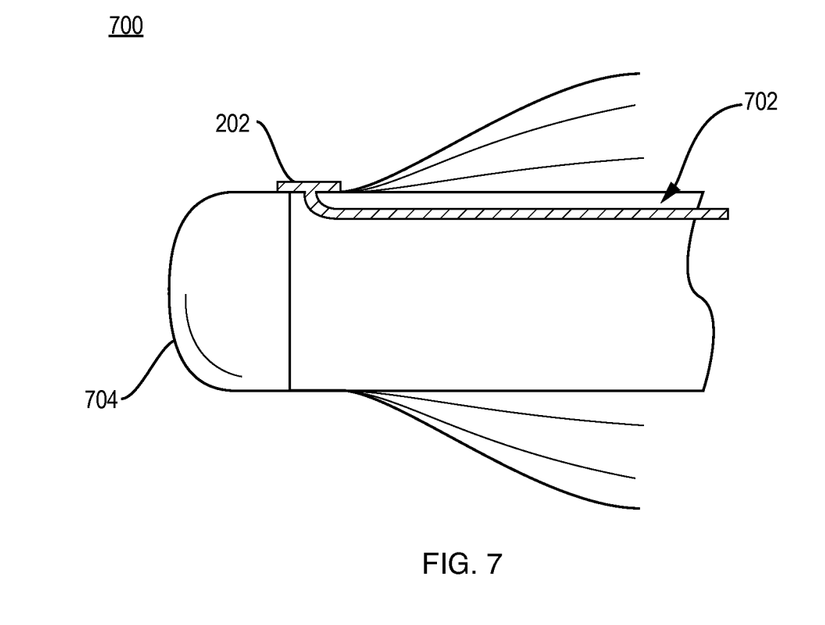
FIG. 7 illustrates an alternative embodiment of the cavity evaluation device or brachytherapy catheter.

FIG. 7 illustrates an alternative embodiment of the cavity evaluation device or brachytherapy catheter (collectively 700). In this alternative embodiment the device 700 includes a non-linear lumen or tubular opening 702 for receiving the guide wire. More particularly, the lumen or tubular opening is characterized by an arcuate turn through approximately 90 degrees such that the anchor member 202 is disposed against a side of the tip 704. One advantage of this embodiment is that the anchor member does not cover the portion of the tip where channels for lumens may be placed.

Figure 8:
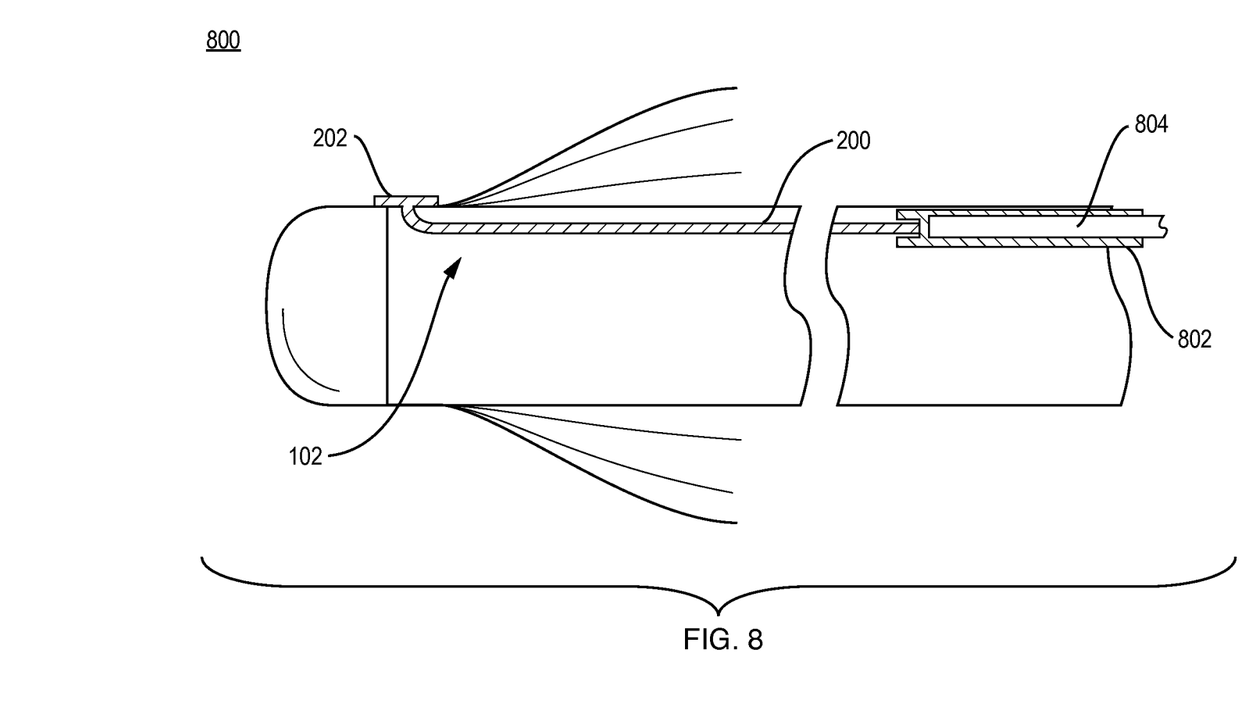
FIGS. 8 and 9 illustrate apparatus for facilitating introduction of the guide member and prevention of contamination.
Figure 9:
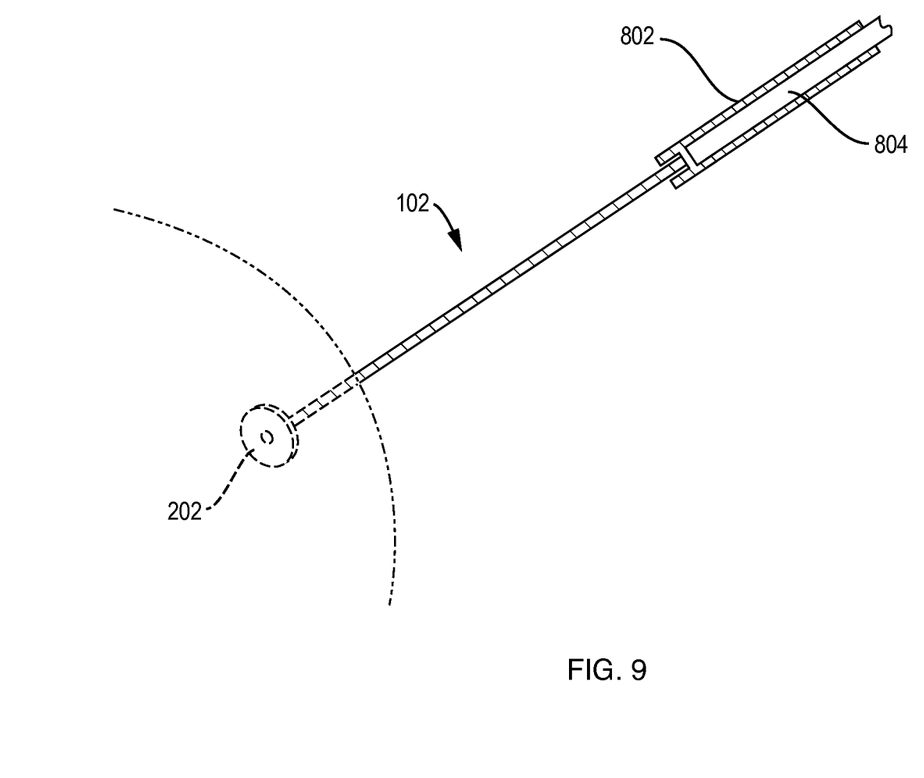

FIGS. 8 and 9 illustrate apparatus for facilitating introduction of the guide member and prevention of contamination. As described above, proper positioning of the anchor member 202 facilitates proper positioning of the brachytherapy catheter 600 and dosing lumens 604. Because soft tissue may present relatively little resistance to removal of the guide member 102 during withdrawal of the cavity evaluation device 100, a separate tool 800 may be used to apply force against the free end of the guide wire 200 as the cavity evaluation device is withdrawn. The tool 800 may include an outer sheath 802 in which a push wire 804 is disposed. The free end of the guide wire is threaded into the sheath and pressure is applied against the guide wire by means of the push wire as the cavity evaluation device is withdrawn. Note that this helps to prevent both movement of the anchor member and contamination of the free end of the guide wire. Moreover, the sheath may be capped and remain in place following removal of the cavity evaluation device and push wire in order to help prevent contamination if the cavity evaluation tool will not be immediately replaced with the brachytherapy catheter.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the invention should not be viewed as limited except by the scope and spirit of the appended claims.

What is claimed is:

1. A method for facilitating brachytherapy treatment comprising the steps of:
positioning a first device such that a distal end of the first device is disposed in a resected cavity of a patient, the first device including a shaft in which is disposed an elongated guide member such that positioning the first device simultaneously positions the elongated guide member, the elongated guide member being configured in which all but a distal end of the elongated guide member is configured to slide relative to the shaft within an interior of the first device, wherein the elongated guide member includes a guide wire and a non-inflatable anchor member at a distal end of the elongated guide member, wherein the non-inflatable anchor member has a curvature and wherein a surface tip of the shaft has an outer curvature that matches the non-inflatable anchor member curvature, and wherein the non-inflatable anchor member curvature is disposed against the surface tip outer curvature when loaded into the first device;
maintaining the non-inflatable anchor member without use of an inflatable device in a fixed position relative to tissue in the resected cavity;
removing the first device from the resected cavity without removing the elongated guide member such that the fixed position of a distal end of the elongated guide member in the resected cavity is maintained relative to the resected cavity; and
introducing the elongated guide member into an opening spanning a length of a brachytherapy catheter and using the elongated guide member to guide the brachytherapy catheter to the resected cavity by moving the brachytherapy catheter relative to the elongated guide member until the brachytherapy catheter envelops all but the distal end of the elongated guide member.

2. The method of claim 1 wherein positioning the first device includes inflating an inflatable member of the first device.

3. The method of claim 2 wherein removing the first device includes deflating the inflatable member.

4. The method of claim 1 wherein the step of removing the first device without removing the guide member includes creating separation between the anchor member and the distal end of the first device.

5. The method of claim 4 including deploying at least a portion of the guide wire from a tubular opening or lumen of the first device.

6. The method of claim 5 including slidably moving the brachytherapy catheter along the guide wire to the extent that the catheter contacts the anchor member.

7. The method of claim 6 including inflating an inflatable member of the brachytherapy catheter after the catheter contacts the anchor member.

8. The method of claim 5 including introducing a free end of the guide member to a sheath and applying force against the free end of the guide member via a push wire.

9. The method of claim 4 wherein the opening is through a side of the brachytherapy catheter.

10. The method of claim 4 wherein the opening is through a most distal portion of the brachytherapy catheter.

11. The method of claim 1, wherein the non-inflatable anchor curvature is substantially concave and wherein the surface tip outer curvature is substantially convex.

12. A system for facilitating and providing brachytherapy treatment, the system comprising:
a first device having:
a distal end disposed in a resected cavity of a patient;
a shaft having an opening within the interior of the first device spanning a length of the first device;
an inflatable member configured to position the first device within the resected cavity when inflated; and
an elongated guide member having a length and a non-inflatable anchor member at a distal end of the guide member, the guide member configured such that all but a distal end of the elongated guide member slide in the opening of the shaft of the first device, the non-inflatable anchor member has a curvature and wherein a surface tip of the shaft has an outer curvature that matches the non-inflatable anchor member curvature, and wherein the non-inflatable anchor member curvature is disposed against the surface tip outer curvature when loaded into the first device, and wherein the non-inflatable anchor member is configured to maintain a fixed position of the distal end of the guide member relative to tissue in the resected cavity without use of an inflatable device even when the elongated guide member is decoupled from the first device; and
a second device separate from the first device, the second device comprising a brachytherapy treatment device comprising a shaft; an inflatable member disposed around the shaft; at least one dosing lumen configured to receive a radiation treatment for brachytherapy treatment; and an opening in the second device spanning a length of the second device and configured to receive the elongated guide member therethrough when the anchor member of the elongated guide member is maintained in the fixed position such that the second device envelops all but the anchor member of the elongated guide member.

13. The system of claim 12, wherein the non-inflatable anchor curvature is substantially concave and wherein the surface tip outer curvature is substantially convex.

* * * * *